United States Patent
Ernst (10) Patent No.: US 6,402,707 B1
(45) Date of Patent: Jun. 11, 2002

(54) METHOD AND SYSTEM FOR REAL TIME INTRA-ORALLY ACQUIRING AND REGISTERING THREE-DIMENSIONAL MEASUREMENTS AND IMAGES OF INTRA-ORAL OBJECTS AND FEATURES

(75) Inventor: Maurice M. Ernst, Jerusalem (IL)

(73) Assignee: Denupp Corporation BVI, Tortolla (VG)

( * ) Notice: Subject to any disclaimer, the term of this patent is extended or adjusted under 35 U.S.C. 154(b) by 0 days.

(21) Appl. No.: 09/605,679

(22) Filed: Jun. 28, 2000

(51) Int. Cl.[7] .......................... A61B 5/103; A61B 5/117
(52) U.S. Cl. .......................... 600/590; 433/214; 433/29
(58) Field of Search .................................. 600/590, 587, 600/414, 417, 425, 426, 443; 433/29, 25, 213, 214, 215

(56) References Cited

U.S. PATENT DOCUMENTS

| | | | |
|---|---|---|---|
| 4,294,544 A | * 10/1981 | Altschuler et al. .......... 356/610 |
| 4,611,288 A | 9/1986 | Duret et al. |
| 4,663,720 A | 5/1987 | Duret et al. |
| 4,821,200 A | 4/1989 | Oberg |
| 4,964,770 A | 10/1990 | Steinbichler et al. |
| 5,237,990 A | 8/1993 | Duret et al. |
| 5,257,184 A | * 10/1993 | Mushabac .................... 433/75 |
| 5,343,391 A | * 8/1994 | Mushabac .................... 433/75 |
| 5,359,511 A | * 10/1994 | Schroeder et al. ............ 433/75 |
| 5,440,393 A | * 8/1995 | Wenz .......................... 600/590 |
| 5,569,578 A | * 10/1996 | Mushabac ................... 433/215 |
| 6,008,905 A | 12/1999 | Breton et al. |

\* cited by examiner

Primary Examiner—Kevin Shaver
Assistant Examiner—Brian Szmal
(74) Attorney, Agent, or Firm—Lilling & Lilling P.C.

(57) ABSTRACT

A method and system for real time intra-orally acquiring and registering three-dimensional measurements and images of intra-oral objects and features. An intra-oral fixed global registration position is established inside the oral cavity of a dental patient, enabling real time acquiring measurements and images of intra-oral objects and features located in multiple fields of view of a measuring and imaging device positioned at various locations in the oral cavity of a dental patient, and recording global positions of the measuring and imaging device relative to the same intra-oral fixed global registration position, where the intra-oral fixed global registration position need not be in any particular field of view of measured and imaged intra-oral objects and features. Local coordinate space pixel positions of acquired and globally recorded measurements and images are registered with global coordinate space pixel positions located in global coordinate space, for forming measurements and images which are all registered with respect to the same intra-oral fixed global registration position in global coordinate space of the oral cavity of the dental patient. Accurate and precise panoramic intra-oral measurement and imaging data and information can be obtained and used in basic and advanced dental applications, whereby measurements and images from multiple fields of view are merged together for forming composite measurements and images, or maps, of the intra-oral objects and features, which can be displayed and stored for further use.

68 Claims, 1 Drawing Sheet

FIG.1

METHOD AND SYSTEM FOR REAL TIME INTRA-ORALLY ACQUIRING AND REGISTERING THREE-DIMENSIONAL MEASUREMENTS AND IMAGES OF INTRA-ORAL OBJECTS AND FEATURES

FIELD AND BACKGROUND OF THE INVENTION

The present invention relates to measuring, imaging, and mapping of intra-oral objects and features and, more particularly, to a method and system for real time intra-orally acquiring and registering three-dimensional measurements and images of intra-oral objects and features, for primary application in the field of dentistry.

Commercial application of non-x-ray based imaging methods, devices, and systems in the field of dentistry, for automatically measuring, imaging, and mapping dental conditions of patients, is still significantly limited, even in view of the current rapid rate of developing and applying a wide variety of non-x-ray based imaging techniques in various other fields. The main objective, and benefit, of using automatic measuring and imaging techniques in dentistry, hereinafter also referred to as 'dental measuring/imaging', is to enable dental practitioners such as dentists, dental hygienists, and dental technicians to obtain highly accurate and precise realistic measurements, images, and spatial maps of intra-oral objects and features such as teeth, gum, intra-oral soft tissue, bone matter, dental undercuts, and, dental fixtures and prostheses of any kind, of dental patients, for the goal of improving procedures and processes, and decreasing costs, relating to examining, charting, diagnosing, and treating dental conditions of those patients.

Details of limitations and shortcomings associated with conventional non-imaging techniques currently used for examining, charting, diagnosing, and treating dental conditions of patients, in general, and for designing, manufacturing, fitting, and monitoring dental prostheses, in particular, are adequately described in dental literature and related prior art, for example, in U.S. Pat. No. 5,440,393, issued to Wenz, in PCT International Publication No. WO 98/52493, in U.S. Pat. No. 5,273,429, issued to Rekow et al., in U.S. Pat. No. 4,964,770, issued to Steinbichler et al., and in U.S. Pat. No. 5,857,853, issued to van Nifterick et al.

A well known example illustrating the potentially significant utility, effectiveness, and, procedural and economic impact of successfully applying automatic measuring and imaging techniques to dentistry involves examining, charting, diagnosing, and treating dental patients requiring dental prostheses such as crowns, bridges, dentures, or implants. More specifically, data and information obtained from measuring, imaging, and mapping intra-oral objects and features can be directly used for highly accurately and cost effectively designing, manufacturing, fitting, and monitoring dental prostheses, thereby replacing currently used inaccurate, labor, material, time, and cost intensive, non-imaging techniques. Automatic dental measuring and imaging techniques are also applicable for performing various types of restorative procedures, occlusal registration, and, orthodontic and tempero mandibular joint (TMJ) dysfunction therapies.

Different categories of mechanisms, such as electrical, electronic, electromechanical, electro-optical, electromagnetic, radar, magnetic, magneto-mechanical, magnetic resonance, acoustic, ultrasound, sonar, photo-acoustic, telemetry, hybrids, and combinations of these, used for automatic three-dimensional measurement, imaging, and mapping of objects, features, and distances, are widely known and employed in various fields. The particular category of electro-optical mechanisms used in measuring and imaging techniques includes, for example, time/light in flight, laser scanning, moire, laser speckle pattern sectioning, interferometry, photogrammetry, laser tracking, and structured light or active triangulation. Specialized interferometric techniques of shearography, diffraction grating, digital wavefront reconstruction and wavelength scanning, and conoscopic holography have recently been developed as useful electro-optical measuring, imaging, and mapping techniques. Electro-optical techniques are reviewed by Chen, F., in "Overview of three-dimensional shape measurement using optical methods", Opt. Eng. 39(1) Jan., 10–22, 2000, and are further described in references therein. Several of these electro-optical techniques have been specifically applied for measuring, imaging, and mapping intra-oral objects and features. Magnetic resonance and ultrasound imaging techniques are well developed and especially applied in the medical field.

Basic in any measuring and imaging technique for accurately and precisely measuring, imaging, or mapping objects and features is the determination, sub-division, and usage of the source space and source resolution associated with the measurements and images. Measurements and images are defined in terms of global and local coordinates of the source space. Global space refers to a global coordinate space, encompassing one or more local coordinate spaces, and is at source resolution. Local space refers to a local coordinate space that is contained within global space that is also at source resolution. Accordingly, by definition, each local coordinate space and all coordinate points or positions contained therein are local with respect to the global coordinate space, whereby they can be transformed, mapped, or related to corresponding global coordinate space and global coordinate points or positions, respectively. This procedure is commonly known as registration of local coordinate space and associated local coordinate points or positions with respect to, or in terms of, global coordinate space and associated global coordinate points or positions, within source space. The registration procedure is performed by using one or more reference, fiducial, or registration, points or markers defined in the global coordinate space, which can also be associated with one or more local coordinate spaces within the global coordinate space.

Hereinafter, the terms 'measuring system', 'measuring device', 'imaging system', and 'imaging device' are general, and are applicable to any category, such as those listed above, of automatic three-dimensional shape measurement, imaging, and mapping of objects and features. With respect to measuring, imaging, and mapping objects and features, the position and orientation of a measuring and imaging device such as an electro-optical measuring and imaging probe, an electromagnetic measuring and imaging probe, an ultrasound measuring and imaging probe, or a magnetic resonance measuring and imaging probe, can be characterized, described, or defined in terms of source or global coordinate space. Furthermore, for each measuring and imaging device global position, each field of view of the measuring and imaging device can be associated with a corresponding local coordinate space, within the source or global coordinate space, where the positions, orientations, and shapes or configurations, of the objects and features in each field of view of the measuring and imaging device are definable in terms of that local coordinate space. Applying a registration procedure here involves transforming or mapping local measurement and image data and information of the objects and features to global measurement and image data and information of the objects and features, using the position and orientation of the measuring and imaging device in global coordinate space as the transforming or mapping common link between global and local coordinate spaces.

Implementation of an automatic measuring and imaging technique usually includes measurement and image processing hardware and software, for automatically performing mathematical operations involved in registering local with global coordinate spaces during and/or after measurement and imaging, and for manipulating and editing measurements and images acquired in local and/or global coordinate spaces. Following these procedures, the graphical or digitized measurements and images are displayed on a display device by converting measurement and image definition from source space into device space, where device space refers to the characteristics of the device, for example, device units or pixels, by which measurements and images are displayed.

In a given automatic measuring and imaging technique, some form of one of the following three methods, object rotation method, measuring and imaging device transport method, and, fixed measuring and imaging system with multiple measuring and imaging devices method, is usually employed for the three-dimensional measuring and imaging of objects and features. In particular, in the measuring and imaging device transport method, registration of coordinate spaces, and, measurement and imaging are typically performed at a number of different fields of view of the measuring and imaging device, according to the desired extent of measuring and imaging the objects and features in the source space. Measurement and image data and information are transformed from local coordinate spaces into the global or source coordinate space using an appropriate registration procedure. Measurements and images are subsequently pieced or merged together, using an appropriate best fit algorithm, for forming composite measurements and images, or maps, of the objects and features of interest, followed by converting measurement and image, and/or map, definition from source space into device space for displaying and/or storing the measurements and images, and/or maps, of the objects and features.

Three-dimensional shape measurement, imaging, and mapping of objects and features, such as intra-oral objects and features, requires the positioning of at least one measuring and imaging device such as an electro-optical measuring and imaging probe, an electromagnetic measuring and imaging probe, an ultrasound measuring and imaging probe, or a magnetic resonance measuring and imaging probe, at different locations within source or global coordinate space, such as the oral cavity or mouth of a dental patient. Accordingly, each global location of the measuring and imaging device is associated with one or more fields of view, where each field of view is characterized or described by a corresponding local coordinate space, within the global coordinate space, and where the positions, orientations, and shapes or configurations, of objects and features of interest such as teeth, gum, intra-oral soft tissue, and dental fixtures or prostheses of any kind, are definable in terms of that local coordinate space.

In order to register point clouds or, measuring and imaging data associated with objects and features located in such local coordinate spaces, in terms of the global coordinate space, each measuring and imaging device coordinate system location and orientation must be accurately and precisely known or measured. Any error in measuring and/or calculating the measuring and imaging device location and orientation causes propagation error in the registration procedure, thereby decreasing accuracy and precision of final output data and information, such as measurements and images, and/or maps, of the particular objects and features of interest.

Various methods are available for enabling the performing of the registration procedure between local and global coordinate spaces, where a particular method used is compatible with a particular measuring and imaging technique, such as those in the above list of categories of automatic three-dimensional shape measurement, imaging, and mapping of objects and features. Commonly used methods for performing the registration procedure are based on: (1) electromechanical location and orientation of the measuring and imaging device, whereby the measuring and imaging device is attached to, or are part of, a highly accurate and precise electromechanical system used for moving and fixing the positions of the measuring and imaging device throughout source or global coordinate space, (2) photogrammetry, also known as pattern recognition, of reference, fiducial, or registration, points or markers accurately located and fixed, and necessarily visible by the measuring and imaging device in the same field of view, or local coordinate space, of the particular objects and features being measured and imaged, (3) optical tracking of each measuring and imaging device location and/or orientation, whereby active or passive optical targets associated with local coordinate spaces defined within source or global coordinate space, are attached to, or part of, each measuring and imaging device, using an optical tracker system, and (4) hybrids of these methods.

Exemplary prior art electro-optical based methods, devices, and systems, each operating with some form of one of the above described registration procedures, for measuring, imaging and mapping intra-oral objects and features, with particular application to dentistry, are briefly summarized below.

In U.S. Pat. No. 4,935,635, issued to O'Harra, there is disclosed a three-dimensional measuring system particularly for dental and other space-limited uses, featuring a laser diode projecting a triangulating beam which scans the surface of intra-oral objects and features, such as a tooth, to be imaged and mapped. Preferably, in a given field of view, three teeth are scanned at a time, with resolution or accuracy of at least fifty microns. The registration procedure is based on the method of electromechanical location and orientation of a mostly extra-orally located imaging device including a probe, highly accurate axial stepping motors, a scanning laser beam, and photodetectors.

In U.S. Pat. No. 4,964,770, issued to Steinbichler et al., there is disclosed a process of making artificial teeth, featuring the use of interferometry, moire and laser scanning imaging methods. Three-dimensional shapes of the ground tooth and of the required artificial tooth are computed in accordance with an optic-geometric formula relating pixel parameters of intensity, background brightness, contrast, and angle. Description is provided for optically imaging only a single ground tooth and non-specific adjacent surfaces. The registration procedure is based on the method of electromechanical location and orientation of components of an extra-orally located imaging system including a light projector, diffraction grating, and a video camera.

In U.S. Pat. No. 5,372,502, issued to Massen et al., there is disclosed an optical probe and method for intra-oral three-dimensional surveying of teeth, including the use of a mobile two-dimensional LCD matrix plate pattern projection unit, optic fibers projecting patterned light beams into the oral cavity, and a CCD matrix image sensor, operating in accordance with moire, phase-shift, triangulation, and photogrammetry techniques. Through a comparison between the undistorted pattern projected by the probe and the distorted pattern reflected from the specific area within the oral cavity, topographical information of the imaged teeth is obtained. A formal registration procedure relating local coordinate spaces of the projected and reflected patterns to source or global coordinate space of the oral cavity is not described in this disclosure, however, it is indicated that instead of using accurately controllable axial mechanical diffraction gratings, supposedly for enabling registration of local coordinate spaces, the surveying procedure is repeated a number of times, whereby accuracy of the imaging data and information is improved by iteration. Overall accuracy and precision of the method are directly dependent upon the extent of simultaneous non-movement of both the optical probe and of the patient during surveying each specific intra-oral region.

In U.S. Pat. No. 5,386,292, issued to Massen et al., there is disclosed a method for correcting imaging errors due to non-optimal reflection qualities of teeth, during three-dimensional optical measurement and imaging of teeth, featuring the use of a light pattern projector and an imaging device such as a CCD matrix image sensor, operating in accordance with moire, phase-shift, and triangulation techniques. Correction is based on determining the angle of incidence of the measuring rays on the surface of a tooth. The registration procedure is based on the method of electromechanical location and orientation of mostly extra-orally located imaging equipment.

In U.S. Pat. No. 5,413,481, issued to Goppel et al., there is disclosed a method and apparatus for manufacturing fitting members, such as for a dental prosthesis, featuring the use of a CCD matrix camera for photographing moire fringes resulting from repeatedly projecting an optical groove grating in a slightly offset manner onto a prepared tooth stump. Description is provided for optically imaging only a single tooth stump. The registration procedure is based on the method of electromechanical location and orientation of components of an essentially extra-orally located imaging system including a projector device, a grating, mirrors, and, stepping motors and springs for fine positional control of the grating.

In U.S. Pat. No. 5,440,393, issued to Wenz, there is disclosed a process and device for measuring the dimensions of a buccal cavity having upper and lower dentition, featuring the use of variable forms of a partly intra-oral optical radiation projection scanning device including light interference and deflection elements, and, an optical signal recording and digitizing system, operating in accordance with photogrammetry, triangulation, and holography techniques. Alternative registration procedures are used, including the method of electromechanical location and orientation of components of the scanning device, and photogrammetry. For photogrammetric registration, the position and orientation of the scanning device are determined relative to the dentition of the buccal cavity, by using an extra-orally located and fixed patient skull frame device supporting three lead balls functioning as reference, or registration, points accurately located and fixed, and necessarily visible by the scanning device, in the same field of view, or local coordinate space, of each image of the buccal cavity.

In U.S. Pat. No. 5,237,998, issued to Duret et al., there is disclosed a method for correlating three-dimensional images of dental arcades, for example, a tooth stump surrounded by two healthy teeth, by correlating intra-oral imaging data of a dental impression of the arcade in the occlusive position with that of the arcade without impression material, where three mutually spaced apart reference points are located and fixed in the immediate vicinity of the arcade. The registration procedure is based on the method of photogrammetry, whereby an intra-oral device featuring a clamp or bar is used for supporting three small spheres functioning as the three reference, or registration, points, accurately located and fixed, and necessarily visible by an imaging device, in the same field of view, or local coordinate space, of every image of the dental arcade.

In U.S. Pat. No. 5,857,853, issued to van Nifterick et al., there is disclosed a method and system for automatically manufacturing a prosthesis to be fixed to implants in the jawbone of a patient, including an intra-oral imaging technique featuring the use of at least one camera positioned at the opened mouth of the patient for three-dimensionally imaging each implant from at least two different oral positions. The registration procedure is based on the method of photogrammetry, whereby 100–150 micron diameter optical recognition points engraved into intra-oral inserts accurately located and fixed onto, and projecting above, each implant, function as the reference, or registration, points, necessarily visible by the camera, in the same field of view, or local coordinate space, of every image of an implant.

To date, the inventor is unaware of a registration procedure based on optical tracking, or based on any type of automatic tracking, featuring wired and/or wireless signal communication mechanisms, of a measuring and imaging device location and/or orientation for implementing a dental measuring and imaging technique.

It is apparent in view of the prior art, that current registration procedures used for implementing dental measuring and imaging techniques are typically based on either electromechanical location and orientation of the measuring and imaging device in source or global coordinate space relative to the intra-oral objects and features being measured or imaged in local coordinate spaces, or, photogrammetry or pattern recognition, of reference, fiducial, or registration, points or markers accurately located and fixed in source or global coordinate space, and necessarily visible by the measuring and imaging device in the same field of view, or local coordinate space, of the particular objects and features being measured or imaged. In general, each of these registration procedures particularly used in dental measuring and imaging has significant limitations, which may be a primary reason for the current relatively worldwide low volume application of non-x-ray based commercial dental measuring and imaging systems.

Electro-mechanical based registration procedures inherently involve the design, manufacture, real time hands-on operation, and maintenance of highly accurate, precise, complex, and expensive, electromechanical devices, mechanisms, components, and elements for enabling proper positional and orientational control of the measuring and imaging device relative to the objects and features of the oral cavity of the dental patient. Moreover, an operator must skillfully, and timely, during a patient visit, adjust the electro-mechanics for re-positioning the measuring and imaging device in order to change fields of view, clearly required for measuring and imaging a plurality, especially a panoramic or complete set, of intra-oral objects and features located throughout the oral cavity of the patient.

A particular limitation of employing electromechanical based registration procedures occurs each time the patient or measuring and imaging device moves immediately prior to or during the measuring and imaging process, whereby, the operator must adjust the electro-mechanics for re-positioning the measuring and imaging device, in order to re-establish the global coordinates of the measuring and imaging device, consequently involving re-registration of local coordinates relative to the new global coordinates.

Photogrammetry or pattern recognition based registration procedures do not require the extent of complex and expensive electromechanical hardware and/or software, however, by definition, the reference, fiducial, or registration, points or markers accurately located and fixed, and necessarily visible by the measuring and imaging device, in the same field of view, or local coordinate space, of one particular set of intra-oral objects and features being measured and imaged, must skillfully, and timely, during a patient visit, be re-positioned in the same field of view of each other particular set of intra-oral objects and features being measured and imaged by an operator. Similar to electromechanical based registration procedures, the re-positioning procedure is clearly required for measuring and imaging a plurality, especially a panoramic or complete set, of intra-oral objects and features located throughout the oral cavity of the patient.

Another particular limitation of employing photogrammetry based registration procedures is that reference, fiducial, or registration, points or markers, need to be of proper color, dimensions and shapes or configurations in order to be properly located, fixed, and distinguishable in a variety of relatively small local coordinate spaces associated with the intra-oral objects and features. Moreover, different colors, sizes and shapes or configurations of the points or markers may need to be used for measuring and imaging the intra-oral objects and features of a single patient, according to the particular intra-oral geometric topography of the patient, and/or according to the extent of dental measuring and imaging needed by the patient.

Additional significant limitations of current dental measuring and imaging techniques in general, which are particularly relevant to the design, manufacture, and fitting, of dental fixtures or prostheses, relate to three-dimensional measuring and measuring and imaging of intra-oral objects and features having one or more undercuts and/or color and shape or structural gradients.

In the field of dentistry, an 'intra-oral undercut', or equivalently, an 'undercut', is properly defined in terms of the following description. If a vertical plane is brought into contact with a curved surface, where the curved surface includes smooth and rough portions, such as the surface of intra-oral objects and features including topological projections, the vertical plane will contact the surface at local maxima points of convexity. If such a curved surface is rotated, while remaining in contact with the vertical plane, an outline is traced corresponding to the maximum perimeter of the curved surface. The region of the curved surface, for example, the region of the surface of intra-oral objects and features, above the outline is referred to as the 'non-undercut' region, and the region below the outline is referred to as the 'undercut' region.

The extent of an intra-oral undercut region varies according to the tilt or angle of the particular intra-oral objects and features in relation to the vertical line. With respect to performing a restorative procedure on intra-oral objects and features, generally, one vertical approach is used for examining and imaging each field of view of the intra-oral objects and features, and subsequently, restoration of the intra-oral objects and features. Therefore, in actuality, as intra-oral objects and features are titled toward or away from each other, an undercut region is essentially always present. For intra-oral objects and features prepared for a restorative procedure, the main strategy is to eliminate undercut regions in restoration preparations by cutting or drilling the target intra-oral objects and features, and filling in undercuts with restorative material, for forming a common 'vertical view', also known as a common 'path of insertion'. In dental practice, however, it is not always possible to perform such ideal restorative preparations.

In dental practice, an undercut can also be referred to as the surface of intra-oral objects and features which, upon removal of set dental impression material from the vicinity of the intra-oral objects and features, causes distortion of the dental impression due to the shape and/or configuration of the undercut, and not due to physicochemical properties of the impression material. Specifically, teeth in normal or treated conditions are usually angled, worn, and/or broken, to varying degrees, causing the presence of undercuts. For example, teeth are typically intentionally drilled down and/or cut by a dental practitioner in order to remove diseased material, such as removal of caries from a tooth, and in preparation of a dental prosthesis.

Intra-oral objects and features, such as teeth, gum, soft tissue, dental fixtures and prostheses of any kind, in normal or treated conditions, are characterized by color and, shape or structural, gradients. Clearly, there exist measuring and imaging limitations, even when applying a dental measuring and imaging technique featuring the use of multiple measuring and imaging devices, caused by the presence of undercuts and, color and shape or structural gradients which need to be addressed for successfully implementing a given dental measuring and imaging technique, in order for information obtained from the measuring and imaging data to be useful to a dental practitioner.

Implementing dental measuring and imaging systems operating with electromechanical or photogrammetric based registration procedures requires working under the above described constrained and limiting conditions. In order to obtain and use accurate and precise panoramic intra-oral measurement and imaging data and information in basic and advanced dental applications, measurements and images from multiple fields of view need to be pieced or merged together, using an appropriate best fit algorithm, for forming composite measurements and images, or maps, of the intra-oral objects and features, usually followed by converting measurements and image, and/or map, definition from source space into device space for displaying and storing the measurements and images, and/or maps, of the intra-oral objects and features. Even for a dental measuring and imaging technique providing high resolution single field of view measurements and images of intra-oral objects and features, any error in measuring and/or calculating locations and/or orientations of the measuring and imaging device relative to the intra-oral objects and features, causes propagation error in the registration procedure, translating to propagation error in the measurement and image piecing or merging procedure, thereby decreasing accuracy, precision, and utility, of final output data and information needed by the dental practitioner.

There is thus a need for, and it would be highly advantageous to have a method and system for real time intra-orally acquiring and registering three-dimensional measurements and images of intra-oral objects and features. Moreover, there is a need for such a method and system which are generally applicable to different categories of techniques of automatic three-dimensional shape measurement, imaging, and mapping of intra-oral objects and features, in the field of dentistry.

SUMMARY OF THE INVENTION

The present invention relates to a method and system for real time intra-orally acquiring and registering three-dimensional measurements and images of intra-oral objects and features.

According to the present invention, there is provided a method for real time intra-orally acquiring and registering three-dimensional measurements and images of intra-oral objects and features, the intra-oral objects and features are located inside the oral cavity of a dental patient, comprising the steps of: (a) establishing an intra-oral fixed global registration position inside the oral cavity of the dental patient, the intra-oral fixed global registration position is definable in terms of global coordinate space of the oral cavity, the global coordinate space is associated with a fixed global reference coordinate system, the global coordinate space includes a plurality of intra-oral local coordinate spaces in the oral cavity; (b) providing a measuring and imaging device for measuring and imaging the intra-oral objects and features located in the oral cavity; (c) selecting a field of view of the measuring and imaging device located at a global position in the global coordinate space of the oral cavity; (d) acquiring at least one three-dimensional measurement and image of the intra-oral objects and features located in the selected field of view of the measuring and imaging device, and, recording the global position of the measuring and imaging device relative to the intra-oral fixed global registration position, for forming at least one globally recorded three-dimensional measurement and image of the intra-oral objects and features located in the oral cavity; (e) repeating step (c) and step (d) for a plurality of said global positions and a plurality of the fields of view of the measuring and imaging device, for forming a plurality of the globally recorded three-dimensional measurements and images of the intra-oral objects and features located in the oral cavity of the dental patient; and (f) registering local coordinate space pixel positions in each of the plurality of globally recorded three-dimensional measurements and images with corresponding global coordinate space pixel positions, for forming a plurality of the three-dimensional measurements and images of the intra-oral objects and features located in the oral cavity of the dental patient which are registered relative to the same intra-oral fixed global registration position.

According to another aspect of the present invention, there is provided a system for real time intra-orally acquiring and registering three-dimensional measurements and images of intra-oral objects and features, where the intra-oral objects and features are located inside the oral cavity of a dental patient, comprising: (a) an intra-oral fixed global registration position inside the oral cavity of the dental patient, the intra-oral fixed global registration position is definable in terms of global coordinate space of the oral cavity, the global coordinate space is associated with a fixed global reference coordinate system, the global coordinate space includes a plurality of intra-oral local coordinate spaces in the oral cavity; (b) a measuring and imaging device for measuring and imaging the intra-oral objects and features located in the oral cavity, relative to the same intra-oral fixed global registration position; and (c) a mobile registration device for measuring and recording global positions and orientations of the measuring and imaging device, relative to the same intra-oral fixed global registration position.

According to further features in preferred embodiments of the invention described below, the intra-oral objects and features are selected from the group consisting of a part or entirety of a combination of teeth, gum, intra-oral soft tissue, bone matter, dental undercuts, and, dental fixtures and dental prostheses, permanent or removable, located inside the oral cavity of the dental patient.

According to further features in preferred embodiments of the invention described below, data and information extractable from the measuring and imaging the intra-oral objects and features located in the oral cavity relative to the same intra-oral fixed global registration position are used in a dental procedure selected from the group consisting of charting an oral condition, diagnosing an oral condition, and treating an oral condition, of the dental patient.

The method and system of the present invention serve as significant improvements over those currently used in the field of dental measuring and imaging, by providing an effective and efficient method and system for acquiring and registering three-dimensional measurements and images of intra-oral objects and features located in multiple fields of view of a measuring and imaging device, which are all registered to the same intra-oral fixed global registration position. This results in eliminating, or at least minimizing, propagation errors relating to piecing and merging together three-dimensional measurement and imaging data and information, especially needed for obtaining highly accurate and precise panoramic measurements and images of intra-oral objects and features located throughout the oral cavity of the dental patient.

Implementation of the method and system of the present invention involves performing or completing selected tasks or steps manually, automatically, or a combination thereof Moreover, according to actual instrumentation and equipment of a particular embodiment, several selected steps of the present invention could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system.

BRIEF DESCRIPTION OF THE DRAWING

The invention is herein described, by way of example only, with reference to the accompanying drawing, wherein.

DESCRIPTION OF THE PREFERRED EMBODIMENTS

The present invention relates to a method and system for real time intra-orally acquiring and registering three-dimensional measurements and images of intra-oral objects and features. Hereinafter, meanings and usage of the terms source space or source coordinate space, global space or global coordinate space, and local space or local coordinate space correspond to commonly known and used meanings and usage of these terms in prior art teachings of measuring, imaging, and mapping. Hence, source space or source coordinate space encompasses both global space or global coordinate space, and, local spaces or local coordinate spaces. Global space or global coordinate space encompasses a plurality of local spaces or local coordinate spaces.

In the description of the present invention, source space or source coordinate space, and, global space or global coordinate space, can both be associated with the same reference coordinate system, whereby the origin, axes, and coordinates of the reference coordinate system are the same for both the source space or source coordinate space and the global space or global coordinate space. For example, source space or source coordinate space, or, global space or global coordinate space can be equivalently used with reference to the space of the oral cavity of a dental patient. Moreover, positions of intra-oral objects and features, such as a part or entirety of any combination of teeth, gum, intra-oral soft tissue, bone matter, dental undercuts, and, dental fixtures and dental prostheses of any kind, permanent or removable, located in a plurality of intra-oral local spaces or intra-oral local coordinate spaces in the oral cavity can be related to, or registered in terms of, source space or source coordinate space, or, global space or global coordinate space, with respect to the previously described reference coordinate system. For clarity and consistency, the terms global space or global coordinate space, and, intra-oral local space or intra-oral local coordinate space, are preferably used throughout the description of the present invention.

Different aspects of novelty of the present invention include, and are based on, the step of establishing an intra-oral fixed global registration position inside the oral cavity of a dental patient. Performing this step enables real time acquiring three-dimensional measurements and images of intra-oral objects and features located in multiple fields of view of a mobile measuring and imaging device moved around, positioned, and orientated at various locations in the oral cavity global space, and recording the various positions and orientations of the measuring and imaging device relative to the same intra-oral fixed global registration position, where the intra-oral fixed global registration position is not limited to being in any particular field of view of measured and imaged intra-oral objects and features.

More specifically, a significant aspect of the novelty here is that of enabling the real time registering of all local coordinate space pixel positions of the acquired and globally recorded three-dimensional measurements and images with global coordinate space pixel positions located in global coordinate space, for forming the three-dimensional measurements and images which are all registered with respect to the same intra-oral fixed global registration position in global coordinate space of the oral cavity of the dental patient. Regardless of the particular category or type of dental measuring and imaging technique applied, the prior art has no teaching of the establishment and use of the same intra-oral fixed global registration position located in global coordinate space inside the oral cavity of a dental patient, for the purpose of registering all local coordinate space pixel positions of all acquired three-dimensional measurements and images of intra-oral objects and features.

Clearly, these novel features lead to significant improvement in obtaining and using accurate and precise panoramic intra-oral measurement and imaging data and information in basic and advanced dental applications, whereby measurements and images from multiple fields of view are merged together for forming composite measurements and images, or maps, of the intra-oral objects and features, followed by converting measurement and image, and/or map, definition from source or global space into device space for displaying, storing, and further using the measurements and images, and/or maps, of the intra-oral objects and features.

It is to be understood that the invention is not limited in its application to the details of construction, arrangement, and composition of the components set forth in the following description, drawings, or examples. For example, the following description features different embodiments of a generalized method and system for real time intra-orally acquiring and registering three-dimensional measurements and images of intra-oral objects and features, in order to illustrate implementation of the present invention. The invention is capable of other embodiments or of being practiced or carried out in various ways. Also, it is to be understood that the phraseology and terminology employed herein are for the purpose of description and should not be regarded as limiting.

Steps, components, operation, and implementation of a method and system for real time intra-orally acquiring and registering three-dimensional measurements and images of intra-oral objects and features, according to the present invention are better understood with reference to the following description and accompanying drawing.

Figure 1:
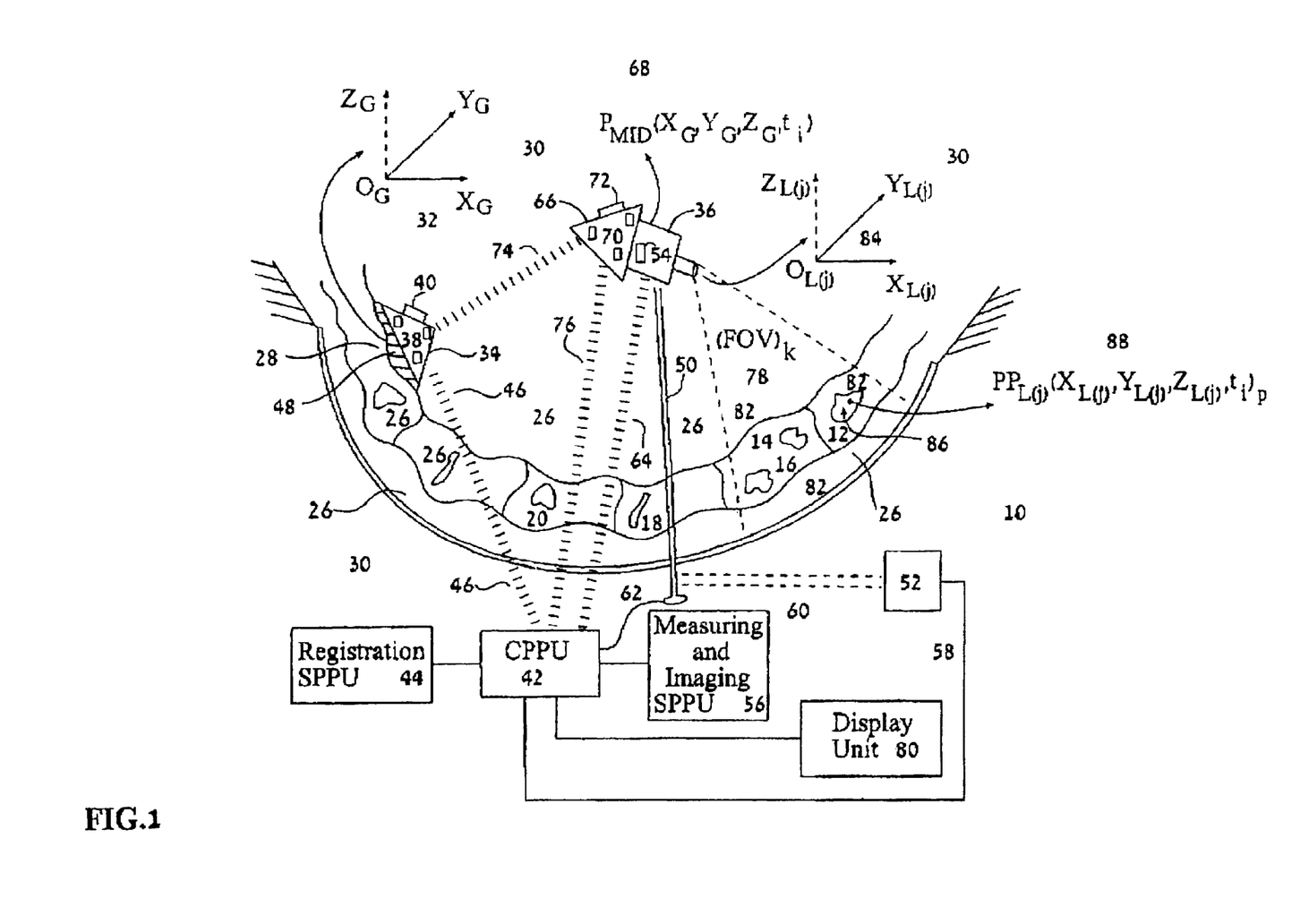
FIG. 1 is a schematic diagram illustrating exemplary preferred embodiments of the system for real time intra-orally registering and acquiring three-dimensional measurements and images of intra-oral objects and features, in accordance with the present invention.

FIG. 1 is a schematic diagram illustrating an exemplary preferred embodiment of the system 10 for real time intra-orally registering and acquiring three-dimensional measurements and images of intra-oral objects and features, such as 12, 14, 16, 18, 20, 22, and 24, where the intra-oral objects and features, such as 12–24, are located inside the oral cavity 26 of a dental patient (not shown). Typical intra-oral objects and features, such as 12–24, are selected from the group consisting of a part or entirety of any combination of teeth, gum, intra-oral soft tissue, bone matter, dental undercuts, and, dental fixtures and dental prostheses of any kind, permanent or removable, located inside oral cavity 26 of the dental patient.

In Step 1 of the method, there is real time establishing an intra-oral fixed global registration position inside the oral cavity of the dental patient. Accordingly, the intra-oral fixed global registration position, for example, 28, is established in terms of global coordinate space 30 of oral cavity 26, of the dental patient. Global coordinate space 30 is associated with a fixed global reference coordinate system, such as fixed global reference orthogonal coordinate system 32, featuring fixed global coordinate system axes, $X_G$-axis, $Y_G$-axis, $Z_G$-axis, and fixed global coordinate system origin, $O_G$. In principle, any other curvilinear coordinate system, for example, a cylindrical, spherical, or hyperbolic, coordinate system, can be used for defining the fixed global reference coordinate system, associated with global coordinate space 30 of oral cavity 26.

Intra-oral fixed global registration position 28, global coordinate space 30, and associated fixed global reference coordinate system 32 are established particularly for defining positions of fixed and/or movable objects, features, devices, instruments, and components, throughout oral cavity 26. However, to accomplish the objectives of the present invention of real time intra-orally registering and acquiring three-dimensional measurements and images of intra-oral objects and features, they are generally applicable for defining positions of fixed and/or movable objects, features, devices, instruments, and components, outside of oral cavity 26.

In sub-step (a), of Step 1, there is providing an intra-oral fixed global registration device 34, used for measuring and determining distances from intra-oral fixed global registration position 28 to a measuring and imaging device, such as 36, further described below. Preferably, physical space or volume occupied by intra-oral fixed global registration device 34 is substantially smaller than total physical space or volume of oral cavity 26 of the dental patient.

Intra-oral fixed global registration device 34 includes a mechanism for sensing or receiving registration signals and responding to registration signals, where a registration signal is any signal relating to the process of registering intra-oral local coordinate space with global coordinate space, as further described below. Additionally, or alternatively, intra-oral fixed global registration device 34 includes a mechanism for transmitting registration signals. Optionally, intra-oral fixed global registration device 34 also includes a mechanism for locally processing sensed or received registration signals, and for locally programming responses to registration signals, and/or, for locally programming transmission of registration signals. For example, a programmed response to a sensed or received registration signal could be in the form of a programmed transmission registration signal. Registration signals can feature any type of analog or digital stimulus, response, and/or data suitable for enabling measuring and recording positions of a measuring and imaging device with respect to intra-oral fixed global registration position 28.

Accordingly, intra-oral fixed global registration device 34 includes at least one, preferably a plurality, of components 38 selected from the group consisting of registration signal sensors, registration signal receivers, registration signal transmitters, and registration signal transceivers. Optionally, intra-oral fixed global registration device 34 also includes a local registration signal programmer and processor (RSPPU) 40, for locally programming and processing registration signals. Intra-oral fixed global registration device 34 in general, and device components 38, optional local registration signal processor and programmer 40, and registration signals, in particular, are designed, configured, and operate according to a category of mechanisms used for measuring distances and recording positions of objects and features selected from the group consisting of electrical, electronic, electromechanical, electro-optical, electromagnetic, radar, magnetic, magneto-mechanical, magnetic resonance, acoustic, ultrasound, sonar, photo-acoustic, telemetry, hybrids, and combinations of these.

Furthermore, intra-oral fixed global registration device 34 in general, and device components 38, optional local registration signal programmer and processor 40, and registration signals, in particular, are designed, configured, and operate according to analog circuitry and/or digital circuitry, and according to a wireless communications mode and/or according to a wired communications mode.

In a preferred embodiment of system 10 featuring a wireless communications mode, intra-oral fixed global registration device 34 is in communication with a central programming and processing unit, for example, CPPU 42, including a registration signal programming and processing unit, RSPPU 44, via a wireless communication link 46, for receiving centralized registration programming and processing data and information from CPPU 42, and for sending local registration programming and processing data and information to CPPU 42. Wireless communication link 46 is preferably, but not limited to, a form of an electromagnetic signal such as a microwave signal, or a sound wave signal.

In an alternative preferred embodiment of system 10 featuring a wired communications mode, intra-oral fixed global registration device 34 is in communication with central programming and processing unit, CPPU 42, including registration signal programming and processing unit, RSPPU 44, via a wired communication link 46, for receiving centralized registration programming and processing data and information from CPPU 42, and for sending local registration programming and processing data and information to CPPU 42. Wired communication link 46 is preferably, but not limited to, a form of an electrical or electronic signal.

In sub-step (b), there is selecting and attaching a substrate for holding intra-oral fixed global registration device 34. Alternatively, intra-oral fixed global registration device 34 features no substrate. In this case, there is continuing the method with sub-step (c), whereby intra-oral fixed global registration device 34 is positioned and fixed directly onto an intra-oral object and/or feature inside oral cavity 26 of the dental patient.

For performing sub-step (b), referring to FIG. 1, a substrate 48 features any suitable single or multi-layered configuration or combination of a composition or material selected from the group consisting of biological components, chemical components, mechanical components, naturally occurring components, synthetically derived components, organic components, and inorganic components, which causes minimal interference with proper operation of intra-oral fixed global registration device 34. For example, substrate 48 features a single component or any combination of an organic chemical such as a plastic, an acrylic, an adhesive or glue, and, an inorganic chemical such as a metallic component such as a screw, a pin, or a clamp, or, a silica based component such as a glass or a ceramic.

In sub-step (c), there is positioning and fixing intra-oral fixed global registration device 34 inside oral cavity 26 of the dental patient. This includes positioning and temporarily fixing intra-oral fixed global registration device 34, either with or without a substrate, for example, substrate 48, to any intra-oral object or feature inside oral cavity 26. In particular, intra-oral fixed global registration device 34 is positioned and temporarily fixed onto any intra-oral object and/or feature, such as any intra-oral object and/or feature 12–24, selected from the group consisting of a part or entirety of any combination of teeth, gum, intra-oral soft tissue, bone matter, dental undercuts, and, dental fixtures and dental prostheses of any kind, permanent or removable, located inside oral cavity 26 of the dental patient.

Intra-oral fixed global registration device 34 is temporarily fixed to any intra-oral object and/or feature 12–24 by using any suitable single or multi-layered configuration or combination of a composition or material selected from the group consisting of biological components, chemical components, mechanical components, naturally occurring components, synthetically derived components, organic components, and inorganic components, which causes minimal interference with proper operation of intra-oral fixed global registration device 34, and, which causes minimal adverse reaction or effect such as irritation, marking, or infection, in oral cavity 26 of the dental patient during the period of time required for the measuring and imaging procedure.

For example, intra-oral fixed global registration device 34 is temporarily fixed to any intra-oral object and/or feature 12–24 by using a single component or combination of an organic chemical such as a plastic, an acrylic, an adhesive or glue, and, an inorganic chemical such as a metallic component such as a screw, a pin, or a clamp, or, a silica based component such as a glass or a ceramic.

Intra-oral fixed global registration device 34 is temporarily fixed to any intra-oral object and/or feature 12–24 in such a way as to remain fixed and rigid with respect to that intra-oral object and/or feature 12–24 during movement or activity of any other object, feature, device, instrument, component, or, the entirety, of oral cavity 26 of the dental patient during the measuring and imaging procedure. Completion of this step enables proper establishment of the intra-oral fixed global registration position, for example, 34, in terms of global coordinate space 30 of oral cavity 26 of the dental patient, where global coordinate space 30 is associated with an intra-oral fixed global reference coordinate system, such as X-axis, Y-axis, Z-axis, intra-oral fixed global reference orthogonal coordinate system 32.

In Step 2, there is providing a measuring and imaging device, for measuring and imaging intra-oral objects and features, and for locally programming and processing measurement and imaging data and information. In FIG. 1, measuring and imaging device 36 includes, among the variety of standard components and mechanisms for enabling measuring, imaging, and mapping, intra-oral objects and features, (i) a position and orientation guide 50, (ii) an optional position and orientation guide automatic controller 52, and (iii) a local measuring and imaging programming and processing unit 54.

Measuring and imaging device 36 is for acquiring three-dimensional measurements and images of the intra-oral objects and features, for example, intra-oral objects and features 12–24, located in oral cavity 26 of the dental patient. Measuring and imaging device 36 is designed and configured for operating either inside or outside of oral cavity 26, for acquiring measurements and images of intra-oral objects and features. For example, according to actual implementation of the present invention, measuring and imaging device 36 may need to be positioned outside of oral cavity 26 in order to effectively measure and image intra-oral objects and features 12–24. Accordingly, measuring and imaging device 36 is not limited to functioning only inside oral cavity 26 of the dental patient.

Position and orientation guide 50 is for three-dimensional maneuvering or guiding, positioning, and orienting measuring and imaging device 36 throughout global coordinate space 30, typically, but not limited to, inside oral cavity 26 of the dental patient.

In a first preferred embodiment of system 10, position and orientation guide 50 is designed, configured, and operates for enabling manual maneuvering or guiding, positioning, and orienting of measuring and imaging device 36 by an operator, such as a dental practitioner. For example, position and orientation guide 50 is a handle or a rod, made of any suitable physicochemical composition or material selected from the group consisting of plastic, glass, and metal components, which causes minimal interference with proper operation of system 10, in general, and of measuring and imaging device 36, in particular, and, which preferably causes no adverse reaction or effect such as irritation, marking, or infection, of oral cavity 26 of the dental patient during the period of time required for the measuring and imaging procedure.

Moreover, in this first embodiment, position and orientation guide 50 features appropriate electromechanical means (not shown), and is in electronic communication with a central programming and processing unit, for example, CPPU 42, including a measuring and imaging signal programming and processing unit, MISPPU 56, via control/data links 58, for receiving centralized measuring and imaging device position and orientation control data and information from CPPU 42, and for sending local position and orientation data and information to CPPU 42.

In a second preferred embodiment, position and orientation guide 50 is designed, configured, and operates for enabling automatic, such as robotic, three-dimensional maneuvering or guiding, positioning, and orienting of measuring and imaging device 36 by an operator, such as a dental practitioner. In this embodiment, position and orientation guide 50 features appropriate electromechanical means (not shown), including electromechanical control/data links 60, for enabling automatic control and communication of position and orientation guide 50 by position and orientation guide automatic controller 52. Moreover, in this second embodiment, position and orientation guide automatic controller 52 is in electronic communication with a central programming and processing unit, for example, CPPU 42, including a measuring and imaging signal programming and processing unit, MISPPU 56, via control/data links 62, for receiving centralized measuring and imaging device position and orientation control data and information from CPPU 42, and for sending local position and orientation data and information to CPPU 42.

Local measuring and imaging programming and processing unit 54 is for locally programming the measuring and imaging of intra-oral objects and features 12–24 by locally controlling activation and operation of measuring and imaging device 36, and is for locally processing measurement and image signals, data, and information relating to intra-oral objects and features 12–24.

Measuring and imaging device 36, in general, and above indicated components 50, 52, 54, 58, 60, and 62, in particular, of measuring and imaging device 36 are designed, configured, and operate according to a category of mechanisms used for automatic three-dimensional shape measurement, imaging, and mapping of objects and features selected from the group consisting of electrical, electronic, electromechanical, electro-optical, electromagnetic, radar, magnetic, magneto-mechanical, magnetic resonance, acoustic, ultrasound, sonar, photo-acoustic, telemetry, hybrids, and combinations of these.

For example, measuring and imaging device 36 operates in the particular category of electro-optical measuring and imaging techniques, according to a technique selected from the group consisting of time/light in flight, laser scanning, moire, laser speckle pattern sectioning, interferometry, photogrammetry, laser tracking, and, structured light or active triangulation. Moreover, measuring and imaging device 36 can also operate according to a specialized interferometric technique such as shearography, diffraction grating, digital wavefront reconstruction and wavelength scanning, or conoscopic holography.

Furthermore, measuring and imaging device 36 in general, device components 50–62, and measuring and imaging signals, in particular, are designed, configured, and operate according to analog circuitry and/or digital circuitry, and according to a wireless communications mode and/or according to a wired communications mode.

In a preferred embodiment of system 10 featuring a wireless communications mode, measuring and imaging device 36 is in communication with a central programming and processing unit, for example, CPPU 42, including a measuring and imaging signal programming and processing unit, MISPPU 56, via a wireless communication link 64, for receiving centralized measuring and imaging programming and processing data and information from CPPU 42, and for sending local measuring and imaging programming and processing data and information to CPPU 42. Wireless communication link 64 is preferably, but not limited to, a form of an electromagnetic signal such as a radio wave signal, a microwave signal, or a sound wave signal.

In an alternative preferred embodiment of system 10 featuring a wired communications mode, measuring and imaging device 36 is in electronic communication with a central programming and processing unit, for example, CPPU 42, including a measuring and imaging signal programming and processing unit, MISPPU 56, via wired control/data links, for example, bundled along or through position and orientation guide 50 and control/data links 62, for receiving centralized measuring and imaging programming and processing data and information from CPPU 42, and for sending local measuring and imaging programming and processing data and information to CPPU 42. The wired communication link is preferably, but not limited to, a form of an electrical or electronic signal.

In Step 3, there is providing a mobile registration device, for enabling measuring and recording global positions and orientations of the measuring and imaging device, 36, relative to the intra-oral fixed global registration position, 28.

In FIG. 1, exemplary mobile registration device 66 is used, in part, for measuring and recording global positions and orientations of measuring and imaging device 36 in global coordinate space 30 of oral cavity 26 of the dental patient, relative to intra-oral fixed global registration position 28, where global coordinate space 30 is associated with fixed global reference orthogonal coordinate system 32, featuring global coordinate system axes, $X_G$-axis, $Y_G$-axis, $Z_G$-axis, and global coordinate system origin, $O_G$. Relative to oral cavity 26, any global position or orientation of measuring and imaging device 36, for example, a $j^{th}$ global position of measuring and imaging device, $P_{MID}$ $(X_G, Y_G, Z_G, t_i)_j$ 68, is describable in terms of global coordinates $X_G$, $Y_G$, $Z_G$, and time, $t_i$, where $t_i$ corresponds to an $i^{th}$ real time value during the performing of the measuring and imaging procedure using system 10.

Mobile registration device 66, in general, and below described components of mobile registration device 66, in particular, are designed, configured, and operate as part of, and/or attached to, and/or separate from, measuring and imaging device 36. As shown in FIG. 1, mobile registration device 66 is preferably attached to measuring and imaging device 36. More preferably, mobile registration device 66 is firmly and rigidly attached to measuring and imaging device 36, in order to attain high accuracy and precision during the process of measuring and recording global positions, $P_{MID}$ $(X_G, Y_G, Z_G, t_i)_j$, of measuring and imaging device 36 in global coordinate space 30, relative to intra-oral fixed global registration position 28.

As indicated above in Step 2, global positions of measuring and imaging device, $P_{MID}$ $(X_G, Y_G, Z_G, t_i)_j$ 68, are typically, but not limited to, intra-oral locations within oral cavity 26 of the dental patient. Accordingly, in the preferred embodiment where mobile registration device 66 is firmly and rigidly attached to measuring and imaging device 36, mobile registration device 66 is not limited to functioning only inside oral cavity 26 of the dental patient. Similar to measuring and imaging device 36, mobile registration device 66 is designed and configured for operating either inside or outside of oral cavity 26.

As shown in FIG. 1, according to the preferred embodiment of system 10, where mobile registration device 66 is firmly attached to measuring and imaging device 36, relative to oral cavity 26, any global position of mobile registration device 66 within global coordinate space 30 is automatically associated with a corresponding global position of measuring and imaging device 36, for example, $j^{th}$ global position of measuring and imaging device, $P_{MID}$ $(X_G, Y_G, Z_G, t_i)_j$ 68. This association of global positions and orientations in global coordinate space 30 between mobile registration device 66 and corresponding global positions of measuring and imaging device 36 enables performing a principle novel step, Step 7 below, of registering or transforming pixel positions of three-dimensional measurements and images initially defined in local coordinate space, relative to a single intra-oral fixed global registration position 28 defined in global coordinate space 30, for forming registered measurements and images of any part or entirety of intra-oral objects and features located in oral cavity 26 of the dental patient.

Mobile registration device 66 includes a mechanism for sensing or receiving registration signals and responding to registration signals. Additionally, or alternatively, mobile registration device 66 includes a mechanism for transmitting registration signals. Optionally, mobile registration device 66 also includes a mechanism for locally processing sensed or received registration signals, and for locally programming responses to registration signals, and/or, for locally programming transmission of registration signals. For example, a programmed response to a sensed or received registration signal could be in the form of a programmed transmission registration signal. Registration signals can feature any type of analog or digital stimulus, response, and/or data suitable for enabling recording of positions of a measuring and imaging device with respect to intra-oral fixed global registration position 28.

Accordingly, mobile registration device 66 includes at least one, preferably a plurality, of components 70 selected from the group consisting of registration signal sensors, registration signal receivers, registration signal transmitters, and registration signal transceivers. Optionally, mobile registration device 66 also includes a local registration signal processor and programmer 72. Mobile registration device 66 in general, and, device components 70, optional local registration signal processor 72, and registration signals, in particular, are designed, configured, and operate according to a category of mechanisms used for measuring distances and registering positions of objects and features selected from the group consisting of electrical, electronic, electromechanical, electro-optical, electromagnetic, radar, magnetic, magneto-mechanical, magnetic resonance, acoustic, ultrasound, sonar, photo-acoustic, telemetry, hybrids, and combinations of these.

Furthermore, mobile registration device 66 in general, and, device components 70, optional local registration signal processor and programmer 72, and registration signals, in particular, are designed, configured, and operate according to analog circuitry and/or digital circuitry, and according to a wireless communications mode and/or according to a wired communications mode.

Referring to FIG. 1, in a preferred embodiment of system 10 featuring a wireless communications mode, mobile registration device 66 is in communication with intra-oral fixed global registration position 28, by communicating with intra-oral fixed global registration device 34 via a wireless communication link 74, for receiving registration signals from intra-oral fixed global registration device 34, and/or for sending registration signals to intra-oral fixed global registration device 34. Wireless communication link 74 is preferably, but not limited to, a form of an electromagnetic signal such as a radio wave signal, a microwave signal, or a sound wave signal.

In an alternative preferred embodiment of system 10 featuring a wired communications mode, mobile registration device 66 is in communication with intra-oral fixed global registration position 28, by communicating with intra-oral fixed global registration device 34 via a wired communication link 74, for receiving registration signals from intra-oral fixed global registration device 34, and/or for sending registration signals to intra-oral fixed global registration device 34. Wired communication link 74 is preferably, but not limited to, a form of an electrical or electronic signal.

In a preferred embodiment of system 10 featuring a wireless communications mode, mobile registration device 66 is in communication with a central programming and processing unit, for example, CPPU 42, including a registration signal programming and processing unit, RSPPU 44, via a wireless communication link 76, for receiving centralized registration processing and programming data and information from CPPU 42, and for sending local registration programming and processing data and information to CPPU 42. Wireless communication link 76 is preferably, but not limited to, a form of an electromagnetic signal such as a radio wave signal, a microwave signal, or a sound wave signal.

In an alternative preferred embodiment of system 10 featuring a wired communications mode, mobile registration device 66 is in communication with a central programming and processing unit, for example, CPPU 42, including a registration signal programming and processing unit, RSPPU 44, via a wired communication link 76, for receiving centralized registration processing and programming data and information from CPPU 42, and for sending local registration programming and processing data and information to CPPU 42. Wired communication link 76 is preferably, but not limited to, a form of an electrical or electronic signal.

In Step 4, there is selecting a field of view of the measuring and imaging device located at a global position in global coordinate space. Referring to FIG. 1, there is selecting a particular field of view, for example, $k^{th}$ field of view, $(FOV)_k$ 78, of measuring and imaging device 36 located at a particular global position, for example, $j^{th}$ global position $P_{MID}$ $(X_G, Y_G, Z_G, t_i)_j$ 68, in global coordinate space 30 of oral cavity 26 of the dental patient. A field of view of measuring and imaging device 36 is selected from the group consisting of fields of view whereby intra-oral fixed global registration position 28 is located outside the field of view, and fields of view whereby intra-oral fixed global registration position 28 is located inside the field of view.

Specifically, as described above with reference to FIG. 1, intra-oral fixed global registration position 28 is defined by a particular fixed location within global coordinate space 30 of oral cavity 26, wherein preferably, physical space or volume occupied by intra-oral fixed global registration device 34 is substantially smaller than total physical space or volume of oral cavity 26 of the dental patient. Accordingly, during operation of system 10, intra-oral fixed global registration position 28 is typically located outside any selected field of view, such as $(FOV)_k$ 78, of measuring and imaging device 36.

For example, in FIG. 1, during real time measuring and imaging intra-oral objects and features 12, 14, and 16, located in $k^{th}$ field of view, $(FOV)_k$ 78, of measuring and imaging device 36, intra-oral fixed global registration position 28 is located outside $k^{th}$ field of view, $(FOV)_k$ 78. In contrast, however, during real time measuring and imaging intra-oral objects and features such as 22 and 24, located in a different (not referenced) $k^{th}$ field of view, $(FOV)_k$, of measuring and imaging device 36 located at a different (not referenced) $j^{th}$ global position, $P_{MID}$ $(X_G, Y_A, Z_G, t_i)_j$, in global coordinate space 30 of oral cavity 26, for example, in the immediate vicinity or behind intra-oral fixed global registration position 28, intra-oral fixed global registration position 28 may be located inside this $k^{th}$ field of view, $(FOV)_k$, of measuring and imaging device 36.

Each field of view, such as exemplary $k^{th}$ field of view, $(FOV)_k$ 78, of measuring and imaging device 36, features any number of intra-oral objects and features, such as 12, 14, and 16, selected from the group consisting of a part or entirety of any combination of teeth, gum, intra-oral soft tissue, bone matter, dental undercuts, and, dental fixtures and dental prostheses of any kind, permanent or removable, located inside oral cavity 26 of the dental patient.

Step 4 is manually or automatically performed by an operator (not shown) of system 10. In particular, in a manual mode of operation, an operator manually holds and moves position and orientation guide 50 for maneuvering measuring and imaging device 36 throughout oral cavity 26 until selecting a desired or target field of view, such as $(FOV)_k$ 78 of intra-oral objects and features such as 12, 14, and 16. In an automatic mode of operation, an operator provides commands to central programming and processing unit, CPPU 42, which communicates with position and orientation guide automatic controller 52 via control/data links 58, for communicating with and automatically controlling position and orientation guide 50 via electromechanical control/data links 60, which in turn communicates with and enables automatic control of positioning and orientation of measuring and imaging device 36. Preferably, during manually or automatically selecting a field of view of measuring and imaging device 36, a display device, for example, as part of a display unit 80, is used for real time displaying measurements, images, data and information relating to and featured in each $k^{th}$ field of view, such as $(FOV)_k$ 78, of measuring and imaging device 36 to the system operator.

In Step 5, there is acquiring at least one three-dimensional measurement and image of the intra-oral objects and features located in the selected field of view of the measuring and imaging device, and recording the global position of the measuring and imaging device relative to the intra-oral fixed global registration position, for forming at least one globally recorded three-dimensional measurement and image of the intra-oral objects and features located in the oral cavity of the dental patient.

In sub-step (a) of Step 5, referring to FIG. 1, there is acquiring at least one three-dimensional measurement and image of intra-oral objects and features 12, 14, and 16 located in exemplary $k^{th}$ field of view, $(FOV)_k$ 78, of measuring and imaging device 36, by activating and operating measuring and imaging device 36, located at a particular global position, for example, $j^{th}$ global position $P_{MID}$ $(X_G, Y_G, Z_G, t_i)_j$ 68, in global coordinate space 30 of oral cavity 26 of the dental patient. This involves central programming and processing unit 42 communicating with local measuring and imaging programming and processing unit 54, preferably, but not limited to, via wireless communication link 64. Following acquiring the at least one three-dimensional measurement and image of intra-oral objects and features 12, 14, and 16, this step further includes storing the at least one three-dimensional measurement and image by central processing and programming unit 42, for example, by operation of measuring and imaging signal processing and programming unit, MISPPU 56.

In sub-step (b), of Step 5, there is recording $j^{th}$ global position $P_{MID}$ $(X_G, Y_G$ I $Z_G, t_i)_j$ 68 of measuring and imaging device 36 relative to intra-oral fixed global registration position 28 in global coordinate space 30 of oral cavity 26 of the dental patient. This involves mobile registration device 66, preferably firmly and rigidly attached to measuring and imaging device 36 and associated with $j^{th}$ global position $P_{MID}$ $(X_G, Y_G, Z_G, t_i)_j$ 68 of measuring and imaging device 36, communicating with intra-oral fixed global registration device 34, preferably, but not limited to, via wireless communication link 74. Following recording $j^{th}$ global position $P_{MID} (X_G, Y_G, Z_G, t_i)_j$ 68 of measuring and imaging device 36 relative to intra-oral fixed global registration position 28 in global coordinate space 30, this step further includes storing the globally recorded position by central processing and programming unit 42, for example, by operation of registration signal processing and programming unit, RSPPU 44.

Sub-steps (a) and (b) of Step 5 are performed synchronously or asynchronously. In particular, sub-step (b) of recording and storing $j^{th}$ global position $P_{MID} (X_G, Y_G, Z_G, t_i)_j$ 68 of measuring and imaging device 36 relative to intra-oral fixed global registration position 28 in global coordinate space 30 is performed at a real time selected from the group consisting of before, simultaneous to, and after, sub-step (a) of acquiring and storing at least one three-dimensional measurement and image of intra-oral objects and features 12, 14, and 16 located in $k^{th}$ field of view $(FOV)_k$ 78 of measuring and imaging device 36. This feature provides operational flexibility for implementing the method and system of the present invention.

In Step 6, there is repeating Steps 4 and 5 for a plurality of global positions and a plurality of fields of view of the measuring and imaging device, for forming a plurality of globally recorded three-dimensional measurements and images of a variety of intra-oral objects and features located throughout the oral cavity of the dental patient.

Referring to FIG. 1, there is repeating Steps 4 and 5 for a plurality of global positions $P_{MID} (X_G, Y_G, Z_G, t_i)_j$, of measuring and imaging device 36, for a pre-determined number of J positions, and for a plurality of fields of view, $(FOV)_k$, of measuring and imaging device 36, for a pre-determined number of K fields of view. This step results in forming a plurality of globally recorded three-dimensional measurements and images of a variety of intra-oral objects and features located throughout oral cavity 26 of the dental patient, which are recorded relative to the same intra-oral fixed global registration position 28.

In Step 7, there is registering local coordinate space pixel positions in each of the plurality of globally recorded three-dimensional measurements and images of the intra-oral objects and features of the oral cavity, relative to the intra-oral fixed global registration position, for forming a plurality of sets of global coordinate space pixel positions, which are registered relative to the same intra-oral fixed global registration point in the oral cavity of the dental patient.

In sub-step (a), of Step 7, there is defining an intra-oral local coordinate space, associated with an intra-oral local reference coordinate system, for each global position of the measuring and imaging device, whereat are globally recorded the plurality of three-dimensional measurements and images of the intra-oral objects and features. In FIG. 1, for example, there is defining intra-oral local coordinate space 82, associated with intra-oral local reference coordinate system 84, featuring local orthogonal reference coordinate system axes, $X_{L(j)}$-axis, $Y_{L(j)}$-axis, $Z_{L(j)}$-axis, and local reference coordinate system origin, $O_{L(j)}$, for each $j^{th}$ global position $P_{MID} (X_G, Y_G, Z_G, t_i)_j$ 68 of measuring and imaging device 36 in global coordinate space 30, whereat is recorded the three-dimensional measurements and images of the intra-oral objects and features, as described in Step 6. In principle, any other curvilinear coordinate system, for example, a cylindrical, spherical, or hyperbolic, coordinate system, can be used for defining intra-oral local reference coordinate system 84, associated with intra-oral local coordinate space 82 of oral cavity 26.

Sub-step (a) provides part of the basis for establishing the necessary spatial and mathematical relationships between local coordinate space pixel positions in a plurality of intra-oral local coordinate spaces, such as 82, and global coordinate space pixel positions in global coordinate space 30, by using each $j^{th}$ global position, $P_{MID} (X_G, Y_G, Z_G, t_i)_j$, such as 68, of measuring and imaging device 36, as the common link between global coordinate space 30 and the plurality of local coordinate spaces therein, needed for registering or transforming local coordinate space pixel positions to global coordinate space 30.

In sub-step (b), of Step 7, there is assigning intra-oral local space coordinates to each intra-oral local coordinate space pixel position, for each of the plurality of globally recorded three-dimensional measurements and images of the intra-oral objects and features. In FIG. 1, for example, there is assigning intra-oral local space orthogonal coordinates, $X_{L(j)}, Y_{L(j)}$, and $Z_{L(j)}$, and, time, $t_i$, to each pixel position, for example, $p^{th}$ pixel position 86, located in intra-oral local coordinate space 82, for each of the previously globally recorded three-dimensional measurements and images of the intra-oral objects and features appearing in one or more fields of view, $(FOV)_k$, for example, $k^{th}$ field of view $(FOV)_k$ 78, for measuring and imaging device 36 located at $j^{th}$ global position $P_{MID} (X_G, Y_G, Z_G, t_i)_j$ 68. Accordingly, each assigned $p^{th}$ pixel position, $(PP_{L(j)})$, is written in terms of intra-oral local space coordinates and time, thus, $PP_{L(j)}(X_{L(j)}, Y_{L(j)}, Z_{L(j)}, t_i)_p$ 88, with reference to the global coordinates via the measuring and imaging device position index, (j). This step further includes storing each assigned local coordinate space pixel position by central programming and processing unit 42.

In sub-step (c), of Step 7, there is transforming the intra-oral local space coordinates of each intra-oral local coordinate space pixel position, in each of the plurality of globally recorded three-dimensional measurements and images of the intra-oral objects and features, to the corresponding or proportionately equivalent global space coordinates, for forming a plurality of sets of global coordinate space pixel positions in global coordinate space which are registered relative to the same intra-oral fixed global registration point.

Referring to FIG. 1, for example, this step involves applying any standard mathematical or algorithmic coordinate space registration technique known in the art, for example, involving matrix transformations, for transforming each local coordinate space pixel position, such as $p^{th}$ pixel position, $PP_{L(j)}(X_{L(j)}, Y_{L(j)}, Z_{L(j)}, t_i)_p$ 88, in each of the intra-oral local coordinate spaces, for example, intra-oral local coordinate space 82, to a corresponding or proportionally equivalent global coordinate space pixel position in global coordinate space 30 of oral cavity 26 of the patient. This is performed for each of the plurality of globally recorded three-dimensional measurements and images of the intra-oral objects and features throughout oral cavity 26 of the dental patient.

This step leads to forming a plurality of sets of global coordinate space pixel positions registered in global coordinate space, which can then be associated with a plurality of three-dimensional measurements and images of the intra-oral objects and features located throughout oral cavity 26 of the dental patient, which are registered relative to same intra-oral fixed global registration point 28 in oral cavity 26 of the dental patient. This step further includes storing the plurality of sets of registered global coordinate space pixel positions by central processing and programming unit 42.

In Step 8, there is using the plurality of sets of registered global coordinate space pixel positions in global coordinate space, which can be associated with a plurality of three-dimensional measurements and images of the intra-oral objects and features located throughout oral cavity 26 of the dental patient, for performing a dental procedure on the dental patient.

Data and information extractable from the sets of registered global coordinate space pixel positions, corresponding to the plurality of globally recorded three-dimensional measurements and images of the intra-oral objects and features located throughout oral cavity 26 of the dental patient, are used in a dental procedure selected from the group consisting of charting an oral condition, diagnosing an oral condition, and treating an oral condition, of the dental patient. Furthermore, the globally recorded and registered three-dimensional measurement and imaging data and information may be used for a type of dental procedure selected from the group consisting of general dental maintenance, dental mapping, dental surgery, dental restoration, orthodontics, periodontics, occlusal registration, and tempero mandibular joint (TMJ) dysfunction therapies.

In particular, the present invention is applicable to dental restoration procedures selected from the group consisting of dental prostheses, such as crowns, bridges, dentures, and/or implants. Moreover, any of the above listed dental procedures may involve any number of intra-oral objects and features selected from the group consisting of a part or entirety of any combination of teeth, gum, intra-oral soft tissue, bone matter, dental undercuts, and, dental fixtures and dental prostheses of any kind, permanent or removable, located inside oral cavity 26 of the dental patient.

For any of the above listed dental procedures involving display of the globally recorded and registered three-dimensional measurement and imaging data and information, Step 8 further includes converting at least one of the globally recorded and registered three-dimensional measurements and images from global space 30 into display device space (not shown), for forming at least one display device measurement and image defined and configured with respect to display device space. The display device measurement and image is subsequently displayed on a display device, for example, as part of display unit 80, as shown in FIG. 1.

An important and novel aspect of the method and system of the present invention is that the intra-oral fixed global registration position is not limited to being inside each field of view of the measuring and imaging device during measuring and imaging intra-oral objects and features, and/or during recording positions and orientations of the measuring and imaging device relative to the intra-oral fixed global registration position. As described above with reference to FIG. 1, the intra-oral fixed global registration position, 28, is defined by a particular fixed location within global coordinate space of the oral cavity of he dental patient, whereby during implementation of the present invention, the intra-oral fixed global registration position is typically located outside fields of view of the measuring and imaging device.

An important consequence of this aspect of the present invention, is that of enabling real time, continuously or discontinuously, acquiring and registering three-dimensional measurements and images of intra-oral objects and features located in multiple fields of view of a mobile measuring and imaging device moved around, positioned, and orientated at various locations throughout global coordinate space of an oral cavity of a dental patient, which are all registered to the same intra-oral fixed global registration position. This results in eliminating, or at least minimizing, propagation errors relating to piecing and merging together three-dimensional measurement and imaging data and information, especially needed for obtaining highly accurate and precise panoramic measurements and images of intra-oral objects and features located throughout the oral cavity of the dental patient.

Regardless of the particular category or type of dental measuring and imaging technique applied, the prior art has no teaching of the establishment and use of a single intra-oral fixed global registration position inside the oral cavity of a dental patient, for the purpose of registering all local coordinate space pixel positions of all the acquired globally recorded three-dimensional measurements and images of intra-oral objects and features to the same intra-oral fixed global registration position. Moreover, the method and system of the present invention are generally applicable to a diversity of techniques of three-dimensional measuring and imaging intra-oral objects and features of dental patients.

While the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method for real time intra-orally acquiring and registering three-dimensional measurements and images of intra-oral objects and features, the intra-oral objects and features are located inside the oral cavity of a dental patient, comprising the steps of:

(a) establishing an intra-oral fixed global registration position inside the oral cavity of the dental patient, said intra-oral fixed global registration position is definable in terms of global coordinate space of the oral cavity, said global coordinate space is associated with a fixed global reference coordinate system, said global coordinate space includes a plurality of intra-oral local coordinate spaces in the oral cavity;

(b) providing a measuring and imaging device for measuring and imaging the intra-oral objects and features located in the oral cavity;

(c) selecting a field of view of said measuring and imaging device located at a global position in said global coordinate space of the oral cavity;

(d) acquiring at least one three-dimensional measurement and image of the intra-oral objects and features located in said selected field of view of said measuring and imaging device, and, recording said global position of said measuring and imaging device relative to said intra-oral fixed global registration position, for forming at least one globally recorded three-dimensional measurement and image of the intra-oral objects and features located in the oral cavity;

(e) repeating step (c) and step (d) for a plurality of said global positions and a plurality of said fields of view of said measuring and imaging device, for forming a plurality of said globally recorded three-dimensional measurements and images of the intra-oral objects and features located in the oral cavity of the dental patient; and (f) registering local coordinate space pixel positions in each of said plurality of globally recorded three-dimensional measurements and images with corresponding global coordinate space pixel positions, for forming a plurality of the three-dimensional measurements and images of the intra-oral objects and features located in the oral cavity of the dental patient which are registered relative to same said intra-oral fixed global registration position.

2. The method of claim 1, wherein the intra-oral objects and features are selected from the group consisting of a part or entirety of a combination of teeth, gum, intra-oral soft tissue, bone matter, dental undercuts, and, dental fixtures and dental prostheses, permanent or removable, located inside the oral cavity of the dental patient.

3. The method of claim 1, wherein said global coordinate space features fixed and movable objects, features, devices, instruments, and components, at a location selected from the group consisting of inside the oral cavity and outside the oral cavity.

4. The method of claim 1, wherein said fixed global reference coordinate system is a curvilinear coordinate system for enabling defining positions in said global coordinate space.

5. The method of claim 1, wherein each of said plurality of intra-oral local coordinate spaces is associated with an intra-oral local reference coordinate system, said intra-oral local reference coordinate system is a curvilinear coordinate system for enabling defining positions in said intra-oral local coordinate space.

6. The method of claim 1, wherein step (a) of establishing an intra-oral fixed global registration position inside the oral cavity of the dental patient, further comprises the steps of:
   (i) providing an intra-oral fixed global registration device for measuring and determining distances of said measuring and imaging device to said intra-oral fixed global registration position;
   (ii) optionally selecting and attaching a substrate for holding said intra-oral fixed global registration device; and
   (iii) positioning and fixing said intra-oral fixed global registration device inside the oral cavity of the dental patient.

7. The method of claim 6, wherein said intra-oral fixed global registration device includes a mechanism selected from the group consisting of sensing or receiving registration signals and responding to registration signals, said registration signals are signals relating to registering said intra-oral local coordinate space with said global coordinate space.

8. The method of claim 6, wherein said intra-oral fixed global registration device includes a mechanism for transmitting registration signals, said registration signals are signals relating to registering said intra-oral local coordinate space with said global coordinate space.

9. The method of claim 6, wherein said intra-oral fixed global registration device includes a mechanism for locally processing registration signals and for locally programming registration signals, said registration signals are signals relating to registering said intra-oral local coordinate space with said global coordinate space.

10. The method of claim 6, wherein said intra-oral fixed global registration device is designed, configured, and operates according to a category of mechanisms used for measuring distances and recording positions of objects and features selected from the group consisting of electrical mechanisms, electronic mechanisms, electro-mechanical mechanisms, electro-optical mechanisms, electromagnetic mechanisms, radar mechanisms, magnetic mechanisms, magneto-mechanical mechanisms, magnetic resonance mechanisms, acoustic mechanisms, ultrasound mechanisms, sonar mechanisms, photo-acoustic mechanisms, telemetry mechanisms, hybrid mechanisms, and combination mechanisms thereof.

11. The method of claim 6, wherein said intra-oral fixed global registration device is designed, configured, and operates according to a combination of mechanisms selected from the group consisting of analog circuitry, digital circuitry, wireless communications modes, and wired communications modes.

12. The method of claim 6, wherein said substrate is selected from the group consisting of a single layered configuration and a multi-layered configuration, said configuration features a material composition selected from the group consisting of biological components, chemical components, mechanical components, naturally occurring components, synthetically derived components, organic components, and inorganic components.

13. The method of claim 6, wherein said intra-oral fixed global registration device is positioned and fixed inside the oral cavity of the dental patient in a form selected from the group consisting of with said substrate and without said substrate.

14. The method of claim 6, wherein said intra-oral fixed global registration device is positioned and fixed on an intra-oral object and feature selected from the group consisting of a part or entirety of a combination of teeth, gum, intra-oral soft tissue, bone matter, dental undercuts, and, dental fixtures and dental prostheses, permanent or removable, located inside the oral cavity of the dental patient.

15. The method of claim 6, wherein said intra-oral fixed global registration device is positioned and fixed inside the oral cavity of the dental patient in a configuration selected from the group consisting of a single layered configuration and a multi-layered configuration, said configuration features a material composition selected from the group consisting of biological components , chemical components, mechanical components, naturally occurring components, synthetically derived components, organic components, and inorganic components.

16. The method of claim 1, wherein said measuring and imaging device is designed and configured for operating at a location selected from the group consisting of inside the oral cavity and outside the oral cavity.

17. The method of claim 1, wherein said measuring and imaging device includes:
   (i) standard components and mechanisms for said measuring and imaging the intra-oral objects and features located in the oral cavity;
   (ii) a position and orientation guide for three-dimensional maneuvering, guiding, positioning, and orienting said measuring and imaging device throughout said global coordinate space selected from the group consisting of inside the oral cavity and outside the oral cavity, of the dental patient;
   (iii) an optional position and orientation guide automatic controller for automatically controlling and communicating with said position and orientation guide; and
   (iv) a local measuring and imaging programming and processing unit for locally programming said measuring and imaging of the intra-oral objects and features by locally controlling activation and operation of said measuring and imaging device, and for locally processing measurement and image signals, data, and information relating to the intra-oral objects and features.

18. The method of claim 1, wherein said measuring and imaging device is designed, configured, and operates according to a category of mechanisms used for three-dimensionally measuring and imaging of objects and features selected from the group consisting of electrical mechanisms, electronic mechanisms, electro-mechanical mechanisms, electro-optical mechanisms, electromagnetic mechanisms, radar mechanisms, magnetic mechanisms, magneto-mechanical mechanisms, magnetic resonance mechanisms, acoustic mechanisms, ultrasound mechanisms, sonar mechanisms, photo-acoustic mechanisms, telemetry mechanisms, hybrid mechanisms, and combination mechanisms thereof.

19. The method of claim 1, wherein said measuring and imaging device is designed, configured, and operates according to a category of electro-optical measuring and imaging techniques selected from the group consisting of time/light in flight, laser scanning, moire, laser speckle pattern sectioning, interferometry, photogrammetry, laser tracking, and, structured light or active triangulation.

20. The method of claim 1, wherein said measuring and imaging device is designed, configured, and operates according to a category of electro-optical measuring and imaging techniques selected from the group consisting of shearography, diffraction grating, digital wavefront reconstruction and wavelength scanning, and conoscopic holography.

21. The method of claim 1, wherein said measuring and imaging device is designed, configured, and operates according to a combination of mechanisms selected from the group consisting of analog circuitry, digital circuitry, wireless communications modes, and wired communications modes.

22. The method of claim 1, wherein said field of view of said measuring and imaging device is selected from the group consisting of fields of view whereby said intra-oral fixed global registration position is located outside said field of view, and fields of view whereby said intra-oral fixed global registration position is located inside said field of view.

23. The method of claim 1, wherein said field of view of said measuring and imaging device includes intra-oral objects and features selected from the group consisting of a part or entirety of a combination of teeth, gum, intra-oral soft tissue, bone matter, dental undercuts, and, dental fixtures and dental prostheses, permanent or removable, located inside oral cavity of the dental patient.

24. The method of claim 1, wherein the step of selecting a field of view of said measuring and imaging device located at a global position in said global coordinate space of the oral cavity is performed in a mode selected from the group consisting of manually selecting said field of view and automatically selecting said field of view.

25. The method of claim 1, wherein, in the step of acquiring at least one three-dimensional measurement and image of the intra-oral objects and features located in said selected field of view of said measuring and imaging device, and, recording said global position of said measuring and imaging device relative to said intra-oral fixed global registration position, said recording said global position of said measuring and imaging device is performed in a mode selected from the group consisting of synchronously and asynchronously with respect to said acquiring said at least one three-dimensional measurement and image.

26. The method of claim 1, wherein the step of recording said global position of said measuring and imaging device relative to said intra-oral fixed global registration position farther comprises the steps of:

(i) providing a mobile registration device for said measuring and recording said global positions and orientations of said measuring and imaging device relative to said intra-oral fixed global registration position;

(ii) associating said global position of said measuring and imaging device with said mobile registration device; and (iii) effecting communication between said mobile registration device and said intra-oral fixed global registration device located at said intra-oral fixed global registration position, said communication features a registration signal with data and information indicating said global position of said measuring and imaging device.

27. The method of claim 26, wherein said mobile registration device includes a mechanism selected from the group consisting of sensing or receiving said registration signals and responding to said registration signals, said registration signals are signals relating to registering said intra-oral local coordinate space with said global coordinate space.

28. The method of claim 26, wherein said mobile registration device includes a mechanism for transmitting registration signals, said registration signals are signals relating to registering said intra-oral local coordinate space with said global coordinate space.

29. The method of claim 26, wherein said mobile registration device includes a mechanism for locally processing said registration signals and for locally programming said registration signals, said registration signals are signals relating to registering said intra-oral local coordinate space with said global coordinate space.

30. The method of claim 26, wherein said mobile registration device is designed, configured, and operates according to a category of mechanisms used for measuring distances and recording positions of objects and features selected from the group consisting of electrical mechanisms, electronic mechanisms, electro-mechanical mechanisms, electro-optical mechanisms, electromagnetic mechanisms, radar mechanisms, magnetic mechanisms, magneto-mechanical mechanisms, magnetic resonance mechanisms, acoustic mechanisms, ultrasound mechanisms, sonar mechanisms, photo-acoustic mechanisms, telemetry mechanisms, hybrid mechanisms, and combination mechanisms thereof.

31. The method of claim 26, wherein said mobile registration device is designed, configured, and operates according to a combination of mechanisms selected from the group consisting of analog circuitry, digital circuitry, wireless communications modes, and wired communications modes.

32. The method of claim 1, wherein the step of registering local coordinate space pixel positions in each of said plurality of globally recorded three-dimensional measurements and images with corresponding global coordinate space pixel positions, further comprises the steps of:

(i) defining an intra-oral local reference coordinate system associated with each said intra-oral local coordinate space, for each said global position of said measuring and imaging device, whereat are said globally recorded plurality of three-dimensional measurements and images of the intra-oral objects and features;

(ii) assigning intra-oral local space coordinates to each said intra-oral local coordinate space pixel position, for each of said plurality of said globally recorded three-dimensional measurements and images of the intra-oral objects and features;

(iii) transforming said intra-oral local space coordinates of each said intra-oral local coordinate space pixel position, in each of said plurality of said globally recorded three-dimensional measurements and images of the intra-oral objects and features, to said corresponding or proportionately equivalent said global space coordinates, for forming a plurality of sets of said global coordinate space pixel positions in said global coordinate space which are registered relative to said same intra-oral fixed global registration point; and (iv) storing said plurality of sets of said global coordinate space pixel positions in said global coordinate space which are registered relative to said same intra-oral fixed global registration point.

33. The method of claim 32, further comprising applying a standard mathematical or algorithmic coordinate space registration technique for performing said transforming said each intra-oral local coordinate space pixel position to said corresponding or proportionally equivalent global coordinate space pixel position located in said global coordinate space of the oral cavity of the patient.

34. The method of claim 1, further comprising the step of:
(g) using said registered global coordinate space pixel positions, associated with said plurality of the three-dimensional measurements and images of the intra-oral objects and features located in the oral cavity of the dental patient, for performing a dental procedure on the dental patient.

35. The method of claim 34, wherein said dental procedure is selected from the group consisting of charting an oral condition, diagnosing an oral condition, and treating an oral condition, of the dental patient.

36. The method of claim 34, wherein said dental procedure is selected from the group consisting of general dental maintenance, dental mapping, dental surgery, dental restoration, orthodontics, periodontics, occlusal registration, and tempero mandibular joint (TMJ) dysfunction therapies, said dental restoration is applicable to dental prostheses selected from the group consisting of crowns, bridges, dentures, and implants.

37. A system for real time intra-orally acquiring and registering three-dimensional measurements and images of intra-oral objects and features, where the intra-oral objects and features are located inside the oral cavity of a dental patient, comprising:

(a) an intra-oral fixed global registration position inside the oral cavity of the dental patient, said intra-oral fixed global registration position is definable in terms of global coordinate space of the oral cavity, said global coordinate space is associated with a fixed global reference coordinate system, said global coordinate space includes a plurality of intra-oral local coordinate spaces in the oral cavity;

(b) a measuring and imaging device for measuring and imaging the intra-oral objects and features located in the oral cavity, relative to same said intra-oral fixed global registration position; and (c) a mobile registration device for measuring and recording global positions and orientations of said measuring and imaging device, relative to same said intra-oral fixed global registration position.

38. The system of claim 37, wherein the intra-oral objects and features are selected from the group consisting of a part or entirety of a combination of teeth, gum, intra-oral soft tissue, bone matter, dental undercuts, and, dental fixtures and dental prostheses, permanent or removable, located inside the oral cavity of the dental patient.

39. The system of claim 37, wherein said global coordinate space features fixed and movable objects, features, devices, instruments, and components, at a location selected from the group consisting of inside the oral cavity and outside the oral cavity.

40. The system of claim 37, wherein said fixed global reference coordinate system is a curvilinear coordinate system for enabling defining positions in said global coordinate space.

41. The system of claim 37, wherein each of said plurality of intra-oral local coordinate spaces is associated with an intra-oral local reference coordinate system, said intra-oral local reference coordinate system is a curvilinear coordinate system for enabling defining positions in said intra-oral local coordinate space.

42. The system of claim 37, wherein said intra-oral fixed global registration position inside the oral cavity of the dental patient, further comprises:

(i) an intra-oral fixed global registration device for measuring and determining distances of said measuring and imaging device to said intra-oral fixed global registration position; and (ii) an optional substrate for holding said intra-oral fixed global registration device.

43. The system of claim 42, wherein said intra-oral fixed global registration device includes a mechanism selected from the group consisting of sensing or receiving registration signals and responding to registration signals, said registration signals are signals relating to registering said intra-oral local coordinate space with said global coordinate space.

44. The system of claim 42, wherein said intra-oral fixed global registration device includes a mechanism for transmitting registration signals, said registration signals are signals relating to registering said intra-oral local coordinate space with said global coordinate space.

45. The system of claim 42, wherein said intra-oral fixed global registration device includes a mechanism for locally processing registration signals and for locally programming registration signals, said registration signals are signals relating to registering said intra-oral local coordinate space with said global coordinate space.

46. The system of claim 42, wherein said intra-oral fixed global registration device is designed, configured, and operates according to a category of mechanisms used for measuring distances and recording positions of objects and features selected from the group consisting of electrical mechanisms, electronic mechanisms, electro-mechanical mechanisms, electro-optical mechanisms, electromagnetic mechanisms, radar mechanisms, magnetic mechanisms, magneto-mechanical mechanisms, magnetic resonance mechanisms, acoustic mechanisms, ultrasound mechanisms, sonar mechanisms, photo-acoustic mechanisms, telemetry mechanisms, hybrid mechanisms, and combination mechanisms thereof.

47. The system of claim 42, wherein said intra-oral fixed global registration device is designed, configured, and operates according to a combination of mechanisms selected from the group consisting of analog circuitry, digital circuitry, wireless communications modes, and wired communications modes.

48. The system of claim 42, wherein said substrate is selected from the group consisting of a single layered configuration and a multi-layered configuration, said configuration features a material composition selected from the group consisting of biological components, chemical components, mechanical components, naturally occurring components, synthetically derived components, organic components, and inorganic components.

49. The system of claim 42, wherein said intra-oral fixed global registration device is adapted to be positioned and fixed inside the oral cavity of the dental patient in a form selected from the group consisting of with said substrate and without said substrate.

50. The system of claim 42, wherein said intra-oral fixed global registration device is adapted to be positioned and fixed on an intra-oral object and feature selected from the group consisting of a part or entirety of a combination of teeth, gum, intra-oral soft tissue, bone matter, dental undercuts, and, dental fixtures and dental prostheses, permanent or removable, located inside the oral cavity of the dental patient.

51. The system of claim 42, wherein said intra-oral fixed global registration device is adapted to be positioned and fixed inside the oral cavity of the dental patient in a configuration selected from the group consisting of a single layered configuration and a multi-layered configuration, said configuration features a material composition selected from the group consisting of biological components, chemical components, mechanical components, naturally occurring components, synthetically derived components, organic components, and inorganic components.

52. The system of claim 37, wherein said measuring and imaging device is designed and configured for operating at a location selected from the group consisting of inside the oral cavity and outside the oral cavity.

53. The system of claim 37, wherein said measuring and imaging device includes:
 (i) standard components and mechanisms for said measuring and imaging the intra-oral objects and features located in the oral cavity;
 (ii) a position and orientation guide for three-dimensional maneuvering, guiding, positioning, and orienting said measuring and imaging device throughout said global coordinate space selected from the group consisting of inside the oral cavity and outside the oral cavity, of the dental patient;
 (iii) an optional position and orientation guide automatic controller for automatically controlling and communicating with said position and orientation guide; and
 (iv) a local measuring and imaging programming and processing unit for locally programming said measuring and imaging of the intra-oral objects and features by locally controlling activation and operation of said measuring and imaging device, and for locally processing measurement and image signals, data, and information relating to the intra-oral objects and features.

54. The system of claim 37, wherein said measuring and imaging device is designed, configured, and operates according to a category of mechanisms used for three-dimensionally measuring and imaging of objects and features selected from the group consisting of electrical mechanisms, electronic mechanisms, electro-mechanical mechanisms, electro-optical mechanisms, electromagnetic mechanisms, radar mechanisms, magnetic mechanisms, magneto-mechanical mechanisms, magnetic resonance mechanisms, acoustic mechanisms, ultrasound mechanisms, sonar mechanisms, photo-acoustic mechanisms, telemetry mechanisms, hybrid mechanisms, and combination mechanisms thereof.

55. The system of claim 37, wherein said measuring and imaging device is designed, configured, and operates according to a category of electro-optical measuring and imaging techniques selected from the group consisting of time/light in flight, laser scanning, moire, laser speckle pattern sectioning, interferometry, photogrammetry, laser tracking, and, structured light or active triangulation.

56. The system of claim 37, wherein said measuring and imaging device is designed, configured, and operates according to a category of electro-optical measuring and imaging techniques selected from the group consisting of shearography, diffraction grating, digital wavefront reconstruction and wavelength scanning, and conoscopic holography.

57. The system of claim 37, wherein said measuring and imaging device is designed, configured, and operates according to a combination of mechanisms selected from the group consisting of analog circuitry, digital circuitry, wireless communications modes, and wired communications modes.

58. The system of claim 37, wherein a field of view of said measuring and imaging device is selected from the group consisting of fields of view whereby said intra-oral fixed global registration position is located outside said field of view, and fields of view whereby said intra-oral fixed global registration position is located inside said field of view.

59. The system of claim 37, wherein a field of view of said measuring and imaging device includes intra-oral objects and features selected from the group consisting of a part or entirety of a combination of teeth, gum, intra-oral soft tissue, bone matter, dental undercuts, and, dental fixtures and dental prostheses, permanent or removable, located inside oral cavity of the dental patient.

60. The system of claim 37, whereby selecting a field of view of said measuring and imaging device located at a said global position in said global coordinate space of the oral cavity is performed in a mode selected from the group consisting of manually selecting said field of view and automatically selecting said field of view.

61. The system of claim 37, whereby acquiring at least one three-dimensional measurement and image of the intra-oral objects and features located in a selected field of view of said measuring and imaging device, and, recording said global position of said measuring and imaging device relative to said same intra-oral fixed global registration position, said recording said global position of said measuring and imaging device is performed in a mode selected from the group consisting of synchronously and asynchronously with respect to said acquiring said at least one three-dimensional measurement and image.

62. The system of claim 37, wherein said mobile registration device includes a mechanism selected from the group consisting of sensing or receiving said registration signals and responding to said registration signals, said registration signals are signals relating to registering said intra-oral local coordinate space with said global coordinate space.

63. The system of claim 37, wherein said mobile registration device includes a mechanism for transmitting registration signals, said registration signals are signals relating to registering said intra-oral local coordinate space with said global coordinate space.

64. The system of claim 37, wherein said mobile registration device includes a mechanism for locally processing said registration signals and for locally programming said registration signals, said registration signals are signals relating to registering said intra-oral local coordinate space with said global coordinate space.

65. The system of claim 37, wherein said mobile registration device is designed, configured, and operates according to a category of mechanisms used for measuring distances and recording positions of objects and features selected from the group consisting of electrical mechanisms, electronic mechanisms, electro-mechanical mechanisms, electro-optical mechanisms, electromagnetic mechanisms, radar mechanisms, magnetic mechanisms, magneto-mechanical mechanisms, magnetic resonance mechanisms, acoustic mechanisms, ultrasound mechanisms, sonar mechanisms, photo-acoustic mechanisms, telemetry mechanisms, hybrid mechanisms, and combination mechanisms thereof.

66. The system of claim 37, wherein said mobile registration device is designed, configured, and operates according to a combination of mechanisms selected from the group consisting of analog circuitry, digital circuitry, wireless communications modes, and wired communications modes.

67. The system of claim 37, wherein data and information extractable from said measuring and imaging the intra-oral objects and features located in the oral cavity relative to said same intra-oral fixed global registration position are used in a dental procedure selected from the group consisting of charting an oral condition, diagnosing an oral condition, and treating an oral condition, of the dental patient.

68. The system of claim 37, wherein data and information extractable from said measuring and imaging the intra-oral objects and features located in the oral cavity relative to said same intra-oral fixed global registration position are used in a dental procedure selected from the group consisting of general dental maintenance, dental mapping, dental surgery, dental restoration, orthodontics, periodontics, occlusal registration, and tempero mandibular joint (TMJ) dysfunction therapies, said dental restoration is applicable to dental prostheses selected from the group consisting of crowns, bridges, dentures, and implants.

* * * * *